United States Patent [19]

Hudson et al.

[11] Patent Number: 5,053,432

[45] Date of Patent: Oct. 1, 1991

[54] NAPHTHOQUINONE DERIVATIVES

[75] Inventors: Alan T. Hudson, Sevenoaks; Anthony W. Randall, Hayes, both of United Kingdom

[73] Assignee: Burroughs Wellcome Co., Research Triangle Park, N.C.

[21] Appl. No.: 456,052

[22] Filed: Dec. 26, 1989

Related U.S. Application Data

[63] Continuation of Ser. No. 891,421, Aug. 1, 1986, abandoned, which is a continuation of Ser. No. 597,379, Apr. 6, 1984, abandoned.

[30] Foreign Application Priority Data

Apr. 14, 1983 [GB] United Kingdom ............... 8310141

[51] Int. Cl.$^5$ ................. A01N 35/00; C07C 50/38
[52] U.S. Cl. ................. 514/682; 514/895; 552/298; 552/299
[58] Field of Search ............ 552/298, 299; 514/682, 514/895

[56] References Cited

U.S. PATENT DOCUMENTS

| | | | |
|---|---|---|---|
| 2,553,648 | 5/1951 | Fieser et al. | 260/396 R |
| 3,206,358 | 9/1965 | Stevenson . | |
| 3,347,742 | 10/1967 | Rogers et al. | 424/331 |
| 3,367,830 | 2/1968 | Sarett . | |
| 3,682,991 | 8/1972 | Tullar et al. . | |
| 4,031,220 | 6/1977 | Richards . | |
| 4,195,089 | 3/1980 | Richards . | |
| 4,485,116 | 11/1984 | Hudson et al. | 260/396 R |
| 4,485,117 | 11/1984 | Hudson et al. | 260/396 R |

FOREIGN PATENT DOCUMENTS

| | | | |
|---|---|---|---|
| 0002228 | 6/1979 | European Pat. Off. | 260/396 R |
| 0077551 | 4/1983 | European Pat. Off. . | |
| 0077550 | 7/1985 | European Pat. Off. . | |
| 2641343 | 4/1977 | Fed. Rep. of Germany . | |

1553424 9/1979 United Kingdom ............... 424/331

OTHER PUBLICATIONS

Fieser, et al., Journal of Medicinal Chemistry, vol. 10, No. 1, Jun. 26, 1967, Naphthoquinone Antimalarials. XXIX, 2-Hydroxy-3-(w-cyclohexylalkyl)-1,4-naphthoquinones, pp. 513–517.

Fieser, et al., vol. 70, pp. 3158-3164, Naphthoquinone Antimalarials. II. Correlation of Structure and Activity Against P. lophurae in Ducks[1].

*Primary Examiner*—C. Warren Ivy
*Assistant Examiner*—Raymond Covington
*Attorney, Agent, or Firm*—Donald Brown; Lawrence A. Nielsen

[57] ABSTRACT

Novel antiprotozoal naphthoquinones having the general formula

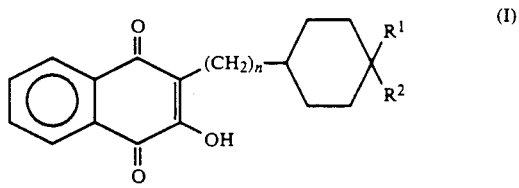

(wherein either $R^1$ is hydrogen and $R^2$ is selected from $C_{1-6}$ alkoxy, aralkoxy, $C_{1-6}$alkyl-$C_{1-6}$alkoxy, phenyl substituted by one or two groups selected from halogen and $C_{1-6}$ alkyl, halogen and perhalo-$C_{1-6}$alkyl; or $R^1$ and $R^2$ are both $C_{1-6}$alkyl or phenyl; and n is 0 or 1) and salt thereof. The compounds of formula (I) are useful for the treatment or prophylaxis of protozoal diseases including malaria, theileriosis and coccidiosis. Various processes for preparing compounds of formula (I) are described.

8 Claims, No Drawings

NAPHTHOQUINONE DERIVATIVES

This is a continuation of copending application Ser. No. 06/891,421 filed on Aug. 1, 1986, now abandoned, which is a continuation of U.S. Ser. No. 06/597,379, filed 4/6/84, now abandoned.

The present invention relates to naphthoquinones and their use in chemotherapy. More specifically the invention is concerned with certain 2-substituted-3-hydroxy-1,4-naphthoquinones, the preparation thereof, formulations thereof and the use thereof in the chemotherapy of human and animal protozoal infections.

2-Substituted-3-hydroxy-1,4-naphthoquinones have previously been described in the art as possessing antiprotozoal activity, in particular antimalarial and, to a lesser extent, anticoccidial activity. Thus Fieser et al. (J. Amer. Chem. Soc. 1948, 70, 3156) disclosed some hundreds of such compounds as possessing antimalarial activity. A number of these, in which a cycloalkyl group was attached to the quinone nucleus, were considered particularly active and were described in U.S. Pat. No. 2,553,648. A number of compounds were administered to man, but these suffered from the disadvantage that large doses were required to achieve an effect. Subsequently attention shifted to compounds having an ω-cyclohexyl alkyl side chain, in particular menoctone, 2-(8-cyclohexyloctyl)-3-hydroxy-1,4-naphthoquinone (e.g. Fieser et al. J. Med. Chem. 1967, 10, 513) but again interest waned because of poor activity in man.

U.S. Pat. No. 3,347,742 taught the use of 2-(4'-cyclohexylcyclohexyl)-1,4-naphthoquinone as an anticoccidial agent but this compound has never achieved practical use.

British Patent Specification No. 1553424 describes 2-hydroxy-3-cyclohexylalkyl and 2-hydroxy-3-cyclohexyl-1,4-naphthoquinone derivatives as effective for the prevention and treatment of theileriosis. European Patent Specification No. 0002228 refers, inter alia to 3-hydroxy-1,4-naphthoquinones in which the substituent in the 2-position is a $C_{3-12}$ cycloalkyl ring optionally substituted by a $C_{1-4}$ alkyl group, in particular a methyl group. However, no such compounds substituted are disclosed, nor is there any indication of which positions of the cycloalkyl ring are to be substituted.

It has now been found that certain novel substituted naphthoquinones as described below exhibit very high activity against one or more protozoa. Thus certain of the compounds exhibit a much higher activity against the human parasite *Plasmodium falciparum* than related compounds previously considered as candidate antimalarial agents. In addition these compounds exhibit good, broad spectrum activity against commercially important Eimeria species, the causative organisms of coccidiosis.

Other of the compounds exhibit a very good activity against theilerial parasites and are notable for their activity against both *T.parvum* and *T.annulata*, exhibiting a higher activity than naphthoquinones previously noted as anti-theilerial agents.

The invention accordingly provides, in a first aspect, compounds of formula (I) and physiologically acceptable salts thereof.

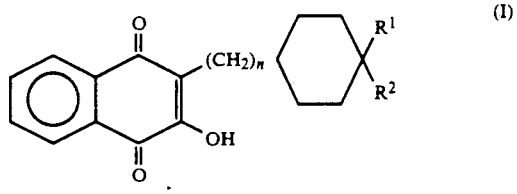

wherein either $R^1$ is hydrogen and $R^2$ is selected from $C_{1-6}$ alkoxy, aralkoxy, $C_{1-6}$alkyl-$C_{1-6}$alkoxy, phenyl substituted by one or two groups selected from halogen and $C_{1-6}$alkyl, halogen and perhalo-$C_{1-6}$ alkyl; or $R^1$ and $R^2$ are both $C_{1-6}$ alkyl or phenyl; and n is 0 or 1.

Since the hydroxyl group in the compounds of formula (I) may form salts with appropriate bases, physiologically acceptable salts include those formed with an alkali metal cation, such as sodium or potassium, and those with organic bases such as ethanolamine, diethanolamine and N-methyl glutamine.

The compounds of formula (I) may exist in a tautomeric form in which the hydroxyl group donates its protons to one of the oxo groups, and such tautomeric forms are included within the scope of this invention. However, it is believed that the form shown in formula (I) is the stable form.

It should be noted that in the unsubstituted 1,4-naphthoquinone ring the 2- and 3-positions are identical and thus, in the naming of the compounds, convention will indicate whether the cyclohexyl substituent or the hydroxyl group is in the 2-position. For convenience, throughout this specification when the compounds are referred to non-specifically, the substituent is defined as in the 2 position.

It will be appreciated that the compounds of formula (I) wherein $R^1$ is hydrogen may exist as cis or trans isomers, that is to say that the cyclohexyl ring may be cis or trans substituted by the naphthoquinone nucleus and the group $R^2$. The invention includes both cis and trans isomers and mixtures thereof in any ratio. In general when the compound is in the form of a mixture of isomers the trans isomer will be present in an amount of about 50% or will be the predominant isomer but mixtures in which the cis isomer predominates are also included within the scope of the invention. The specific ratio of isomers may be varied as required; typical mixtures include those in which the cis/trans isomer ratio is about 1:1, 40:60 and 5:95.

Within the scope of formula (I) are compounds of formula (IA).

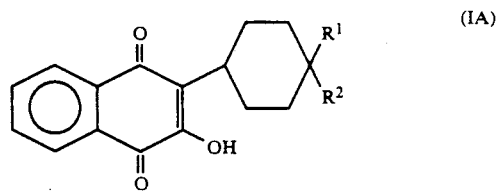

wherein $R^1$ and $R^2$ are as defined above.

The compounds of formula (IA) are of particular interest as antimalarial agents and anticoccidial agents.

Also within the scope of formula (I) are compounds of formula (IB)

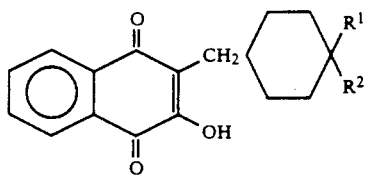

(IB)

where $R^1$ and $R^2$ are as defined above.

Compounds of formula (IB) are of particular interest as antitheilerial agents. Compounds of formula (IB) are also of value as intermediates in the preparation of compounds of formula (IA) above.

Within the compounds of formula (I) preferred compounds include those wherein:
(a) $R^1$ is hydrogen and $R^2$ is
 (i) $C_{1-6}$ alkoxy, for example methoxy, n-butoxy and t-butoxy;
 (ii) aralkoxy, wherein the alkyl moiety has from 1 to 6 carbon atoms, for example benzyloxy; the aryl moiety, e.g. phenyl, may optionally bear one or more substituents, for example halogen (e.g. chlorine);
 (iii) $C_{1-6}$alkyl-$C_{1-6}$alkoxy wherein the alkyl moiety is straight or branched, for example methylene, isopropylene and the alkoxy moiety is straight chain, for example methoxy;
 (iv) phenyl bearing one or two substituents selected from halogen, e.g. chlorine, and $C_{1-6}$ alkyl, e.g. methyl, preferably in the 3 and/or 4 position(s);
 (v) halogen, for example fluoro;
 (vi) perfluoro $C_{1-6}$alkyl, for example trifluoromethyl.

Specific compounds included within the scope of formula (I) include:

2-hydroxy-3-(4-methoxycyclohexyl)-1,4-naphthoquinone;

2-hydroxy-3-[4-(1-methoxy-1-methylethyl)cyclohexyl]-1,4-naphthoquinone;

2-(4-benzyloxycyclohexyl)-3-hydroxy-1,4-naphthoquinone;

2,4-(4-chlorophenyl)cyclohexyl-3-hydroxy-1,4-naphthoquinone;

2,4-(3,4-dichlorophenyl)cyclohexyl-3-hydroxy-1,4-naphthoquinone;

2-[4-(3,4-dimethylphenyl)cyclohexyl]-1,4-naphthoquinone;

2-(4-fluorocyclohexyl)-3-hydroxy-1,4-naphthoquinone;

2-hydroxy-3-(4-trifluoromethylcyclohexyl)-1,4-naphthoquinone;

2-(4-n-butoxycyclohexyl)-3-hydroxy-1,4-naphthoquinone;

2-(4-t-butoxycyclohexyl)-3-hydroxy-1,4-naphthoquinone;

2-(4,4-dimethylcyclohexyl)-3-hydroxy-1,4-naphthoquinone;

2-(4,4-diethylcyclohexyl)-3-hydroxy-1,4-naphthoquinone;

2-(4,4-diphenylcyclohexyl)-3-hydroxy-1,4-naphthoquinone;

2-(4,4-di-n-propylcyclohexyl)-3-hydroxy-1,4-naphthoquinone and

2-[4-(4-chlorophenoxymethyl)cyclohexyl]-3-hydroxy-1,4-naphthoquinone.

According to a further feature of the present invention we provide compounds of formula (I) (as defined above) and physiologically acceptable salts thereof for use as therapeutic agents, for example, for use in the treatment or prophylaxis of a protozoal disease in an animal, e.g. man.

According to a further feature of the present invention we provide a method for the treatment or prophylaxis of a protozoal disease in an animal which comprises administering to the animal an anti-protozoal amount of a compound of formula (I) or a physiologically acceptable salt thereof.

The compounds of formula (IA) have been found to be extremely active against the human malaria parasite *Plasmodium falciparum* and are thus of use in the treatment and/or prophylaxis of malaria in man. The compounds of formula (IA) have also been found to be extremely active against protozoa causing the commercially important forms of coccidiosis, in particular *Eimeria tenella* and *E. acervulina* and are thus of use in the treatment or prophylaxis of coccidiosis in animals, particularly birds.

It will be appreciated that the amount of compound of formula (IA) required for use in treatment or prophylaxis will vary not only with the active compound but also with the route of administration and nature of the infection or condition. In general a suitable dose for a mammal (including man) for treatment, for example of malaria, will lie in the range of 0.1 mg to 200 mg per kilogram bodyweight per day, with a preferred range of 1 mg to 100 mg/kg, particularly 10 mg to 40 mg/kg. For the prophylaxis or treatment of coccidiosis the compound will normally be administered ad lib in drinking water or diet and suitable levels of drug will be in the range of 1 to 500 ppm, preferably 10–400 ppm, ideally about 200 ppm.

The compounds of formula (IB) have been found to be extremely active against protozoa of the genus Theileria, and are thus of use in the treatment and/or prophylaxis of theileriosis in cattle and sheep. In particular the compounds have been found to be active against infection by *T.annulata* or *T.parva*.

It will be appreciated that the amount of compound of formula (IB) required for use in the treatment or prophylaxis of theilerial infections will vary not only with the active compound, but also with the route of administration and nature of the infection.

The "effective amount, dosage or unit-dosage" as used herein is denoted to mean a predetermined amount of the compound which is sufficiently effective against protozoal organisms, for instance in cattle or sheep when administered in vivo. To contribute to or achieve prophylaxis or cure, some preparations may contain multiples of the dosage required by a single animal.

A typical initial dose for cattle weighing 400 kg may be 0.2 to 10 g conveniently 0.5 to 2.5 g, and for calves or sheep 50 mg to 1.0 g, or preferably about 0.1 to 0.5 gramme of the active compound, but further dosages may be given.

The compounds of formula (I) are preferably presented as a therapeutic (pharmaceutical or veterinary) formulation.

Therapeutic formulations comprise at least one compound of formula (I) on a physiologically acceptable salt thereof together with one or more pharmaceutically acceptable carriers therefor and optionally other therapeutic and/or prophylactic ingredients. The carrier(s) must be 'acceptable' in the sense of being compatible with the other ingredients of the formula and not deleterious to the recipient thereof.

The active compound(s) may conveniently be presented (as a pharmaceutical formulation) in unit dosage form. A convenient unit dose formulation contains the active ingredient compound(s) in an amount of from 10 mg to 1 g.

Therapeutic formulations include those suitable for oral, rectal or parenteral (including intramuscular and intravenous) administration, although oral is the preferred route. The formulations may, where appropriate, be conveniently presented in discrete dosage units and may be prepared by any of the methods known in the art of pharmacy. All methods include the step of bringing into association the active compound with liquid carriers or finely divided solid carriers of both and then, if necessary, shaping the product into the desired formulation.

Therapeutic formulations suitable for oral administration wherein the carrier is a solid are most preferably presented as unit dose formulations such as boluses, capsules, cachets or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface-active or dispersing agent. Moulded tablets may be made by moulding an inert liquid diluent. Tablets may be optionally coated and, if uncoated, may optionally be scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope. Therapeutic formulations suitable for oral administration wherein the carrier is a liquid may be presented as a solution or a suspension in an aqueous liquid or a non-aqueous liquid, or as an oil-in-water or water-in-oil liquid emulsion.

Therapeutic formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping moulds.

Therapeutic formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface-active agents, thickeners, lubricants, preservatives (including anti-oxidants) and the like, and substances included for the purpose of rendering the formulation isotonic with the blood of the intended recipient.

The therapeutic formulations for veterinary use, in particular for coccidiosis, may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the active ingredient(s), and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound of formula (I) or a salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The compounds of the present invention may also be used in combination with other therapeutic agents, for example other antiprotozoal agents. In particular the compounds of the invention may be employed together with known antimalarial, anticoccidial and/or antitheilerial agents.

The invention thus provides, in a further aspect, a combination comprising a compound of formula (I) as defined herein or a pharmaceutically acceptable salt thereof together with another therapeutically active agent, in particular an antimalarial or anticoccidial agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The combinations defined above, in particular when a second antimalarial or anticoccidial agent is employed, are of value inter alia in delaying the onset of resistance to the compounds of formula (I).

Suitable therapeutic agents for use in the mixtures defined above include, for example, pyrimethamine, chloroquine, mefloquine, quinine, primaquine, monensin, halofuginone, arprinocid and zoalene.

When compounds of formula (I) are used in combination with a second therapeutic agent effective against the same parasites the dose of each compound will vary from that when the compound is used alone. Appropriate doses may be readily determined by those skilled in the art.

The compounds of formula (I) may be prepared in conventional manner, e.g. using processes described in the literature.

According to a further feature of the present invention we provide a process for the preparation of compounds of formula (I) and physiologically acceptable salts thereof which comprises a) hydrolysing the corresponding 3-X-substituted compound (wherein X represents a group which is hydrolysable to a hydroxy group) or the corresponding 2,3-epoxide;

b) oxidising a compound of formula (II)

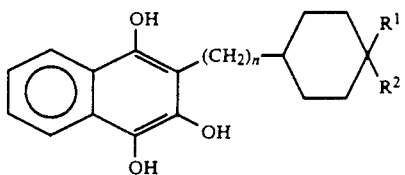

(wherein n, R¹ and R² are as hereinbefore defined);

c) reacting a compound of formula (III)

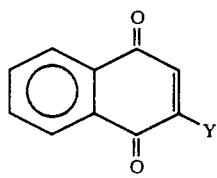

(wherein Y represents a hydroxy group or a group hydrolysable thereto) with a donor compound providing the R¹ and R²-substituted-cyclohexyl or cyclohexylmethyl residue wherein R¹ and R² are as hereinbefore defined and (when Y represents a hydrolysable group) hydrolysing the said group to a hydroxy group;

d) converting a compound of formula (I) (wherein n is 1) to a corresponding compound of formula (I) (wherein n is 0) by Hooker oxidation; and optionally converting a resulting compound of formula (I) into a physiologically acceptable salt thereof;

e) converting a compound of formula (IV).

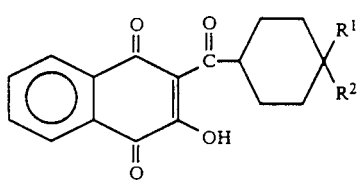

wherein R¹ and R² are as defined previously, to a compound of formula (IB) by reduction of the oxomethyl group, e.g. by hydrogenation especially under pressure and in the presence of a catalyst, for example a copper chromite catalyst.

With regard to process a), compounds of formula (I) may be prepared by, for example, converting the corresponding 3-halogeno, e.g. 3-chloro or 3-bromo, analogues of formula (V)

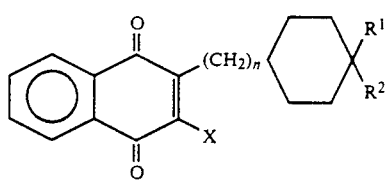

wherein R¹, R² and n are as defined in formula (I) and X is halogen, into the corresponding 3-hydroxy compound by alkaline hydrolysis, for example with an alkali metal hydroxide in a suitable medium, for instance potassium hydroxide in aqueous methanolic medium has been found convenient.

The compounds of formula (V) above are novel compounds and thus provide a further aspect of the invention. The compounds of formula (II) may be prepared by methods known in the art for the preparation of compounds of analogous structure, for example the method described by Fieser, L., J. Am. Chem. Soc., 1948, 3165 et seq.

Other hydrolysable groups which may be present in the 3-position of the starting materials include acyloxy groups, e.g. $C_{1-4}$ alkanoyloxy groups such as acetoxy, or aroyl groups such as benzyloxy; and $C_{1-6}$ alkoxy groups such as methoxy.

Also with regard to process a), the 2,3-epoxide of formula (VI)

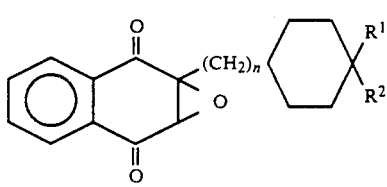

may be hydrolysed to a compound of formula (I) for example with dilute aqueous acid or dilute aqueous base.

The compounds of formula (V) and (VI) above may be prepared for example by halogenation or expoxidation respectively in conventional manner of a compound of formula

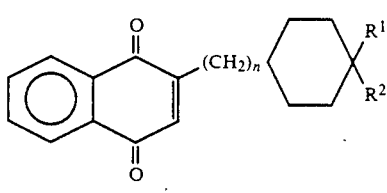

(wherein n, R¹ and R² are as defined hereinabove).

Compounds of formula (VII) may also be subjected to a Thiele acetylation by reaction with an appropriate acetylating agent (e.g. acetic anhydride) in the presence of an oxidising agent (e.g. perchloric acid) to provide compounds of formula (IIa). Compounds of formula (IIa) may be converted to compounds of formula (IIb) by hydrolysis which compounds may be converted to compounds of formula (I) by oxidation in accordance with process b), e.g. by a method analogous to that described in Organic Reactions, Vol 19, p. 222. Suitable oxidising agents include, for example, ferric chloride and a mineral acid or chromic acid.

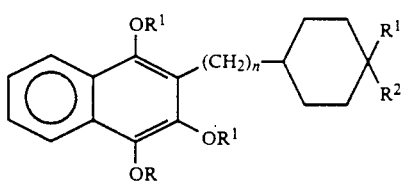

a) R¹ = COCH₃
b) R¹ = H

In process c) the hydrolysable group Y in formula (III) may be a group as defined for X in process a) above, for example halo, e.g. chloro or bromo, or a hydroxy, acetoxy or $C_{1-6}$alkoxy group.

The donor compound in process c) is generally a compound which is capable of providing the substituted cyclohexyl or cyclohexylmethyl group as a free radical with the electron in the correct position vis-a-vis the t-alkyl substituent either spontaneously or under oxidising conditions.

A suitable donor compound is the corresponding cycloalkane carboxylic acid which may undergo oxidative decarboxylation. For instance persulphate with a catalyst, such as silver ions, is convenient for the purpose, (c.f. Jacobson, N., et al., Annalen, 1972, 763, 135 and Acta Chem. Scand, 1973, 27, 3211). Preferably, when persulphate is used under these conditions, the reaction is carried out with a 1,4-naphthoquinone in which Y is other than hydroxy. Conveniently ammonium persulphate can be used as the oxidising agent, and the catalyst is silver nitrate. Hydrolysis subsequent to the main coupling reaction may, if required, provide the hydroxy group. Alkaline conditions are usually preferred for the hydrolysis.

An example of the donor itself carrying a peroxide grouping is the method employing an appropriately substituted cycloalkanoyl peroxide as suggested by U.S. Pat. No. 2,553,647.

The provision of the cycloalkyl free radical by a spontaneous release from the donor can, for instance, be achieved by the use of a tricycloalkylborane. Such reagent can easily be prepared by reacting the cycloalkene with borane dimethylsulphide. Conveniently the reaction is carried out in a solvent such as tetrahydrofuran.

Other possible cyclohexyl or cyclohexylmethyl donors include appropriately substituted cyclohexenyl or cyclohexenylmethyl carboxylic acids. In such cases the resulting condensate will additionally require reduction to provide a compound of formula (I).

It will be appreciated to those skilled in the art that the processes described herein may lead either to isomeric mixtures (cis and trans) of the compounds of formula (I), or, where isomerically pure starting material is employed, to pure cis or trans compounds of formula (I).

It has been found that the non-stereospecific preparative methods generally lead to an approximately 1:1 ratio of the cis and trans isomers, the amount of trans isomer in the recovered product may be increased by adjustment of reaction conditions, in particular by selection of a solvent system in which the trans isomer is less soluble. Such solvent systems may be readily determined by experiment but a solvent system found to be particularly effective is a mixture of water and acetonitrile. By use of such systems cis to trans ratios of from about 2:3 to about 1:4 may be obtained.

Where a single isomer, cis or trans, is desired this may be obtained by stereospecific synthesis, e.g. by Hooker Oxidation as described above or by separation of the isomers by physical means. Such methods are well known in the art and include, for example, fractional crystallisation or chromatographic separation.

With regard to process d), the compounds according to formula (IA) may be prepared from the corresponding compound of formula (IB) by Hooker oxidation as described for example in J. Am. Chem. Soc., 1948, 3174 or 3215.

The present invention also includes bioprecursors for the compounds of formula (I) above e.g. compounds of formula

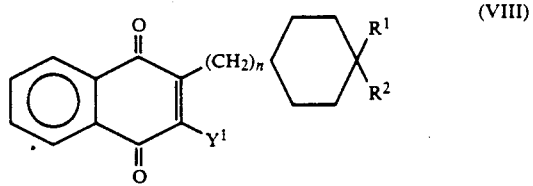

wherein $R^1$, $R^2$ and n are as defined in formula (I) above and $Y^1$ is a halogeno, acetoxy, benzoyloxy or $C_{1-6}$alkoxy group. These are novel compounds and are useful as intermediates in the syntheses described above. Those which carry a group for $Y^1$ which is easily hydrolysed in vivo into the hydroxy group, may be used as pro-drugs in formulations or for treatment to provide the hydrolysed end-product in situ. The acetyl or benzoyl group may undergo such hydrolysis and thus these bioprecursors are of potential as long acting precursors of active compounds.

The following examples illustrate the invention:

EXAMPLE 1

2-Hydroxy-3-(4-methoxycyclohexyl)-1,4-naphthoquinone

A mixture of 2-chloro-1,4-naphthoquinone (1.16 g), 4-methoxycyclohexane-1-carboxylic acid (1.3 g) and silver nitrate (0.3 g) were stirred at 65° C. in a mixture of acetonitrile (2.5 ml), sulpholane (7.5 ml) and water (17.5 ml) while a solution of ammonium persulphate (2.3 g) in water (5 ml) was added dropwise during 15 minutes. The reaction mixture was stirred for a further 15 minutes at 65° C., cooled in ice and extracted with ether. The ether extracts were washed with sodium bicarbonate solution, dried and evaporated. The crude product was recrystallised from acetonitrile to yield 2-chloro-3-(4-methoxycyclohexyl)-1,4-naphthoquinone, m.p. 110°–113° C.; the product so obtained (0.9 g) was dissolved in boiling methanol (25 ml) and a solution of potassium hydroxide (0.9 g) in water (9 ml) added dropwise during 10 minutes. The reaction mixture was then refluxed for a further 30 minutes, concentrated hydrochloric acid (5 ml) added dropwise and the mixture cooled in ice. Addition of an equal volume of water precipitated an oil which slowly turned to a semi-solid. Recrystallisation from acetonitrile yielded 2-hydroxy-3-(4-methoxycyclohexyl)-1,4-naphthoquinone, m.p. 152°–155°, shown by n.m.r. to be the pure trans isomer.

EXAMPLES 2 TO 15

By a method analogous to that of Example 1 the following compounds of formula (I) were prepared. Unless otherwise stated the compounds of Examples 2 to 11 were a mixture of cis and trans isomers.

| Example No. | $R^1$ | $R^2$ | | m.pt./°C. |
|---|---|---|---|---|
| 2 | Me–C(–OCH$_3$)–Me | H | | 152–155° |
| 3 | OCH$_2$Ph | H | | 98–103° |
| 4 | 4-ClPh | H | (trans) | 216–219° |
| 5 | 3,4-Cl$_2$Ph | H | (trans) | 202–204° |
| 6 | 3,4-Me$_2$Ph | H | (trans) | 161–164° |
| 7 | F | H | | 118–120° |
| 8 | CF$_3$ | H | (trans) | 185–187° |

-continued

| Example No. | R¹ | R² | | m.pt./°C. |
|---|---|---|---|---|
| 9 | O(CH₂)₃CH₃ | H | (trans) | 76–78° |
| 10 | OC(CH₃)₃ | H | (trans) | 161–164° |
| 11 | CH₂O(4ClPh) | H | (stereochemistry unknown) | 125–128° |
| 12 | Me | Me | | 134–136° |
| 13 | Et | Et | | 118–119.5° |
| 14 | Ph | Ph | | 218–219° |
| 15 | (CH₂)₂CH₃ | (CH₂)₂CH₃ | | 144–146° |

EXAMPLE 16

Preparation of Substituted Cyclohexane Carboxylic Acid Intermediates

A number of the substituted cyclohexane carboxylic acids used in Examples 1 to 15 are novel; their preparation is described below:

A. Preparation of 4-Trifluoromethylcyclohexane-1-carboxylic Acid

Ethyl 4-trifluoromethylbenzoate (4.9 g) was dissolved in ethanol (60 ml) and catalyst (5% rhodium on alumina, 0.5 g) added. Reduction with hydrogen gas was effected at ambient temperature at 50 atmospheres pressure until the theoretical quantity of hydrogen had been absorbed. The catalyst was removed by filtration through "hyflo" filter aid and the solvent was removed by evaporation to provide crude ethyl 4-trifluoromethylcyclohexane-1-carboxylate.

The crude ethyl ester from above (3.35 g) was mixed with water (7 ml), methanol (2.6 ml) and potassium hydroxide (2.02 g). The mixture was heated on a steam bath for 90 minutes and then poured onto water (20 ml). The mixture was washed once with pentane and then the aqueous layer adjusted to pH 2 with concentrated hydrochloric acid. The solid product was collected by filtration, washed with ice-water and dried to give 4-trifluoromethylcyclohexane-1-carboxylic acid m.pt. complete at 110° C.

Similarly prepared were:
4-methoxycyclohexane-1-carboxylic acid, b.p. 102°–108° C. (at 0.2 mmHg); and
4-n-butoxycyclohexane-1-carboxylic acid, b.p. 134°–144° C. (at 0.2 mmHg).

B. Preparation of 4-Benzyloxycyclohexyl-1-carboxylic acid

4-Benzyloxycyclohexan-1-one (4.1 g) and "TOSMIC" (4.24 g) were dissolved in dry dimethoxyethane (70 ml) and dry ethanol (3 ml). The mixture was stirred at 0° C. while potassium-t-butoxide (5.4 g) was added in portions over 15 minutes. The reaction mixture was then stirred at 0° C. for 15 minutes and ambient temperature for 2 hours, diluted with saturated sodium chloride solution (250 ml) and extracted with chloroform (3×100 ml). The organic extracts were combined, washed with water, dried (using MgSO₄) and evaporated to give an orange oil.

The crude 4-benzyloxycyclohexane-1-nitrile (4.0 g) was refluxed with stirring with a mixture of glacial acetic acid (16 ml) and concentrated hydrochloric acid (24 ml) for 20 hours. The reaction mixture was cooled, the solid removed by filtration and washed with water. The product was ground with 2M sodium hydroxide solution (70 ml) and then diluted with water. Unchanged nitrile was removed by filtration and the filtrate acidified with concentrated hydrochloric acid. White crystals separated and were collected by filtration, washed with water and dried to yield 4-benzyloxycyclohexane-1-carboxylic acid m.p. 170°–180° C.

Similarly prepared were:
4-(1-methyl-1-methoxyethyl)-cyclohexane-1-carboxylic acid, m.p. 55°–64° C. and
4-(4-chlorophenoxymethyl)-cyclohexane-1-carboxylic acid, m.p. 112°–115° C. (cis isomer 193°–196° C. (trans isomer).

C. Preparation of 4-(4-Chlorophenyl)cyclohexane-1-carboxylic Acid

Acetyl chloride (30 g) and finely powdered aluminium chloride (60 g) were stirred together in carbon disulphide (120 ml) and then cooled to −50° C. in a CO₂/oxitol bath. Cyclohexene (30 g), previously cooled to −50° C., was added dropwise during 10 minutes while maintaining the temperature of the reaction mixture at below −20° C. The mixture was stirred at −50° C. for a further 60 minutes and the solvent then decanted to leave a gummy orange complex. A little chlorobenzene was added as the material warmed to ambient temperature; the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodium hydroxide and water, dried over anhydrous sodium sulphate and evaporated to dryness. The product was distilled in vacuo, the fraction boiling at 140°–154° C. (0.1 mm Hg) collected, diluted with an equal volume of petroleum ether (40–60), cooled to −6° C. and a continuous stream of nitrogen gas bubbled through, and the separated colourless solid recovered.

Bromine (2.8 ml) was added to a solution of sodium hydroxide (6.2 g) in water (42 ml) at 0° C. The above-obtained substituted hexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite was added to destroy excess hypobromite, the mixture cooled and then acidified to give a colourless solid. The solid was filtered off, washed with water, dried and recrystallised from ethanol to give 4-(4-chlorophenyl)cyclohexane-1-carboxylic acid, m.p. 254°–256° C.

Similarly prepared were:
4-(3,4-dichlorophenyl)cyclohexane-1-carboxylic acid m.p. 181°–183° C. and
4-(3,4-dimethylphenyl)cyclohexane-1-carboxylic acid m.p. 169°–170° C.

D. Preparation of 4-Fluorocyclohexyl-1-carboxylic Acid

A mixture of ethyl 4-hydroxycyclohexyl-1-carboxylic acid (21 g) and sodium fluoride (7.8 g) in pyridine/HF reagent (70%; 200 ml) was stirred at ambient temperature for 8 hours, poured onto ice water and extracted with diethyl ether. The ether extracts were washed with water and sodium bicarbonate solution until all excess HF had been neutralised, dried (using Na₂SO₄) and the solvent removed by evaporation. The crude product was purified by distillation to give ethyl- 4-fluorocyclohexane-1-carboxylate (b.p. 94°-96° C./14 mm Hg).

The ethyl ester (1.4 g) in methanol (3 ml) and a solution of potassium hydroxide (0.9 g) in water (5 ml) was heated on a steam bath for 5 hours, the reaction mixture poured onto ice/water and washed with petroleum ether (60-80). The aqueous phase was acidified with hydrochloric acid, extracted with chloroform and the organic extracts dried and evaporated to dryness to give 4-fluorocyclohexane-1-carboxylic acid which was used without further purification.

E. Preparation of 4-t-Butoxycyclohexane-1-carboxylic Acid

Ethyl 4-hydroxycyclohexane-1-carboxylate (17 g) was dissolved in methylene dichloride (250 ml) and conc. sulphuric acid (1 ml) added. A stream of isobutene was passed in for 8 hours. The mixture was washed thoroughly with sodium bicarbonate solution, dried and evaporated to a mixture of oil and solid.

Ether was added to dissolve most of the material and the solids removed by filtration. The ethereal filtrate was evaporated and the residue distilled (b.p. 76°-80° C./0.4 mm Hg) to give a partially crystalline product. The solid, m.p. 95°-112° C., was separated from the oil by filtration and proved to be a polymer of isobutene. The filtrate was ethyl 4-t-butoxycyclohexane-1-carboxylate.

The ethyl 4-t-butoxycyclohexane-1-carboxylate (1 g), thus obtained, was heated on a steam bath with 2M sodium hydroxide solution (10 ml) to which had been added ethanol (2 ml). After about 4 hours a homogenous solution had formed. The reaction mixture was washed with petroleum ether (60-80) and the aqueous phase acidified with concentrated hydrochloric acid. An oil separated which crystallised on cooling and scratching. The solid was collected and recrystallised from petroleum ether (60-80) to yield 4-t-butoxycyclohexane-1-carboxylic acid, m.pt. 100°-105° C.

F. Preparation of 4,4-Diphenylcyclohexane-1-carboxylic Acid 4,4-Diphenylcyclohexan-1-one (1.25 g) was suspended in acetic acid (2 ml) and stirred at 0° C., while a solution of sodium cyanide (0.7 g) in water (2 ml) was added dropwise. The reaction mixture was stirred at ambient temperature overnight and then partitioned between chloroform and water. The organic layer was separated, washed with water, dried (using $MgSO_4$), evaporated to dryness and the oil so obtained triturated with cold toluene. The white solid obtained was collected, washed with cold toluene and petroleum ether (40-60) and dried.

The above product (10.73 g) was dissolved in dry pyridine (9.75 ml) and dry benzene (9.75 ml), stirred at 0° C. and a solution of phosphorylchloride (12.7 ml) in pyridine (11.7 ml) added dropwise over 45 minutes. The mixture was slowly warmed to reflux during 45 minutes and then refluxed for a further 30 minutes. The hot solution was poured carefully onto crushed ice (200 ml) with stirring which was continued for 30 minutes. The mixture was extracted with chloroform (2×100 ml), the organic extracts washed with water, dried (using $MgSO_4$) and evaporated to dryness to give a yellow solid.

The nitrile (9.0 g), potassium hydroxide (6.4 g), ethanol (8.0 ml) and water (10 ml) were refluxed for 48 hours. The reaction mixture was acidified with concentrated hydrochloric acid and diluted with water (200 ml). The white solid which formed was extracted with ethyl acetate (2×200 ml), the organic extracts washed with water and then extracted with 1M sodium hydroxide (200 ml).

The aqueous extract was acidified with concentrated hydrochloric acid and the white precipitate collected, washed with water, dried and recrystallised from ethanol to give 4,4-diphenylcyclohex-1-ene-1-carboxylic acid (m.p. 227°-229° C.).

The acid (4.5 g) was dissolved in ethanol (200 ml) and catalyst (10% Pd/C, 0.45 g) added under nitrogen. The mixture was hydrogenated at 50° C./4 atm. for 5 hours. The catalyst was removed and the filtrate evaporated to dryness to give 4-4-diphenylcyclohexane-1-carboxylic acid, m.p. 191°-192° C.

Similarly prepared were:

4,4-dimethylcyclohexane-1-carboxylic acid, m.p. 39°-42° C.

4,4-diethylcyclohexane-1-carboxylic acid, m.p. 44°-46° C.

4,4-di-n-propylcyclohexane-1-carboxylic acid, m.p. 98°-102° C.

EXAMPLE 17A

Activity of 2-(substituted cyclohexyl)-3-hydroxynaphthoquinones against *Plasmodium falciparum* in vitro Compounds of formula (IA), as hereinbefore described, were examined for their inhibitory effect on *Plasmodium falciparum* in vitro.

The test method was a modification of that described by Desjardins et al., Antimicrob. Agents and Chemotherapy, 1979, 16, 710-718. Compounds were dissolved in ethanol at a concentration of 1000 mg/L and dilutions down to 1 mg/L were made. The drug solutions were serially diluted using RPMI 1640 medium+10% human plasma in microtitration plates. Parasitised and fresh red blood cells were added, together with G-$^3$H-hypoxanthine, in RPMI 1640 medium+10% human plasma and the cultures incubated for 36 hours. Cultures were then harvested, the particulate contents collected on a glass fibre filter paper and washed copiously with water. The filter papers were dried and the radioactivity measured using a scintillation counter. Infected untreated and uninfected untreated cultures were included as controls.

The results are shown in Table I.

EXAMPLE 17B

Activity of 2-(substituted cyclohexyl)-3-hydroxynaphthoquinones against *P.yoelii* in vivo The naphthoquinone was suspended in 0.25% (w/v) celacol in water by milling for 16-24 hours at 26° C. The suspensions were subsequently serially diluted with 0.25% (w/v) celacol in water.

At time 0, 0.1 ml of a suspension of $10^7$ *P.yoelii*-parasitised red blood cells/ml of phosphate saline were injected intravenously into 15-20 g mice through a tail vein. Groups of 5 mice per treatment were dosed orally at times 6, 22, 30, 54, 70 and 78 hours with 0.2 ml of the drug suspension. Tail-blood smears were taken at 96 hours, stained with Giemsa and the percentage of red blood cells infected determined and compared to untreated, infected controls. Percent inhibition was correllated with dose to provide $ED_{50}$ values. The results are shown in Table IA below.

TABLE I

| $R^1$ | $R_2$ | Dose (mg/L) | % Inhibition |
|---|---|---|---|
| OMe | H | 0.0625 | 70 |
| $C(CH_3)_2OCH_3$ | H | 0.0156 | 47 |
| $OCH_2Ph$ | H | 0.0625 | 62 |
| 4-ClPh | H | 0.00625 | 55 |
| 3,4-Cl$_2$Ph | H | 0.00125 | 49 |
| 3,4-Me$_2$Ph | H | 0.001 | 47 |
| F | H | 0.0625 | 51 |
| $CF_3$ | H | 0.0313 | 62 |
| $O(CH_2)_3CH_3$ | H | 0.0156 | 52 |
| $OC(CH_3)_3$ | H | 0.000032 | 48 |
| $CH_2OPh$-4Cl | H | [$IC_{50}$ = 0.16] | |
| $CH_3$ | $CH_3$ | 0.00625 | 48 |
| Et | Et | 0.0078 | 64 |
| Ph | Ph | 0.0625 | 48 |
| nPr | nPr | 0.00156 | 52 |

TABLE IA

| Compound of formula (I) $R^1$ | $R^2$ | $ED_{50}$ (mg/kg × 7) |
|---|---|---|
| $C(CH_3)_2OCH_3$ | H | 1.95 |
| $OCH_2Ph$ | H | 2.5 |
| 4-Cl.Ph | H | 0.0625 |
| 3,4-Cl$_2$Ph | H | 0.1275 |
| 3,4-Me$_2$Ph | H | 0.0169 |
| $CF_3$ | H | 1.0 |
| $O(CH_2)_2CH_3$ | H | 0.475 |
| $OC(CH_3)_3$ | H | 0.25 |
| $CH_3$ | $CH_3$ | 15 |
| $C_2H_5$ | $C_2H_5$ | 1.188 |
| nPr | nPr | 3.0 |
| $CH_3$ | $CH_3$ | 0.00625 | 48 |
| Et | Et | 0.0078 | 64 |
| Ph | Ph | 0.0625 | 48 |
| nPr | nPr | 0.00156 | 52 |

Menoctone [2-(8-cyclohexyloctyl)-3-hydroxy-1,4-naphthoquinone] was found to have an $ED_{50}$ of $2.55 \times 10^{-7}$ against *P. falciparum in vitro*.

EXAMPLE 18

Activity of 2-(substituted cyclohexyl)-3-hydroxy-naphthoquinone against Eimeria species Certain of the compounds tested in Example 17 were assayed for their activity against *E. tenella*. In the method employed, cell cultures were infected with sporozoite suspensions of *E. tenella* immediately after addition of the compounds. Serial dilutions of solutions of the compounds were made as in Example 17 in a range of concentrations of 19 µg/l to 20 mg/l in order to determine the minimum inhibitory concentration (MIC). After incubation for 96 hours the cultures were fixed and the cells were stained with 0.1% toluidine blue. The stained cultures were examined microscopically for presence of parasites. The results obtained are shown in Table 2.

TABLE 2

| $R^1$ | $R^2$ | MIC(mg/L) |
|---|---|---|
| $C(CH_3)_2OCH_3$ | H | 0.125 |
| $OCH_2Ph$ | H | 0.31 |
| 4-Cl-Ph | H | 0.31 |
| 3,4-Cl$_2$Ph | H | 1.25 |
| 3,4-Me$_2$Ph | H | 0.078 |
| F | H | 0.31 |
| $CF_3$ | H | 0.005 |
| $CH_3$ | H | 0.031-0.0031 |

TABLE 2-continued

| $R^1$ | $R^2$ | MIC(mg/L) |
|---|---|---|
| $C_2H_5$ | $C_2H_5$ | 0.0125 |
| Ph | Ph | 1.25 |
| nPr | nPr | 0.031-0.0031 |

EXAMPLE 19

A. In vitro activity against *T. parva*

In vitro results demonstrating the effectiveness of the compounds of formula (IA) against *T. parva* are shown below. Cultures of bovine lymphoblastoid cells infected with the macroschizont stage of *T. parva* were incubated for 48 hours in the presence of various concentrations of compounds of formula (I). Other cultures were incubated without the drug to act as controls. Fourfold dilutions of compounds were assayed to determine $ED_{50}$ values, at least two tests being conducted on each compound. The $ED_{50}$ is the concentration of drug required (mg/L) to reduce the proportion of schizont-infected cells of the culture to 50% of that of untreated controls in the 48 hr incubation period.

The results are given in Table 3.

TABLE 3

| $R^1$ | $R^2$ | $ED_{50}$(mg/L) |
|---|---|---|
| $C(CH_3)_2.OCH_3$ | H | 0.006 |
| $OCH_2Ph$ | H | 0.1 |
| 4-ClPh | H | 0.01 |
| 3,4-Cl$_2$Ph | H | 0.1 |
| F | H | 0.01 |
| $CF_3$ | H | 0.0015 |
| $OC(CH_3)_3$ | H | 0.006 |
| $CH_3$ | $CH_3$ | 0.0015 |
| $C_2H_5$ | $C_2H_5$ | 0.0125 |
| Ph | Ph | >1.0 |
| nPr | nPr | 0.01 |

EXAMPLE 20

Formulations

"Pour-on" Formulation

A "pour-on" formulation for cattle may be prepared as follows:

| Compound of formula (I) | 4 parts by weight |
|---|---|
| Dimethyl sulphoxide | 10 parts by weight |
| Castor oil | to 100 parts by weight |

Aqueous Suspension

An aqueous suspension may be prepared as follows:

| Compound of (I) | 1.00 part by weight |
|---|---|
| Neosyl | 16.00 parts by weight |
| Bentonite | 3.20 parts by weight |
| Glycerin | 15.00 parts by weight |
| Sodium benzoate | 1.00 part by weight |
| Bevaloid 35/2 | 1.00 part by weight |
| Thymol | 0.04 parts by weight |
| Water | 62.76 parts by weight |
| | 100.00 |

Salt Block

A salt block may be prepared by mixing a finely divided compound of formula (I) (0.5 parts by weight)

with sodium chloride (99.5 parts by weight) and the mixture pressed into blocks.

Paste

The following paste may be prepared:

| Compound of formula I | 3.0 parts by weight |
|---|---|
| Gum tragacanth | 4.0 parts by weight |
| Bevaloid 35/3 | 1.0 part by weight |
| Nipagin "M" | 0.1 parts by weight |
| Glycerin | 19.0 parts by weight |
| Water | 72.9 parts by weight |
| | 100.0 |

Injectable Solution

A solution for subcutaneous injection may be prepared by mixing:

| Compound of formula (I) | 4.5 parts by weight |
|---|---|
| Methocel | 2.0 parts by weight |
| Nipagin "M" | 0.1 parts by weight |
| Water | 93.4 parts by weight |
| | 100.0 |

Injectable Solution

A solution for intramuscular injection may be prepared by mixing:

| Compound of formula (I) | 9.5 parts by weight |
|---|---|
| Dimethyl sulphoxide | 19.0 parts by weight |
| Sorbitan monooleate | 4.5 parts by weight |
| Corn oil | 67.0 parts by weight |
| | 100.0 |

Injectable Solution

The following injectable formulation was prepared:

| Compound of formula (I) | 5 parts by weight |
|---|---|
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

Tablet Formulation

| Compound of formula (I) | 100 mg |
|---|---|
| Lactose | 100 mg |
| Maize starch | 30 mg |
| Magnesium stearate | 2 mg |
| | 232 mg |

Oral Suspension

| Compound of formula I | 50 mg |
|---|---|
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |

| -continued | |
|---|---|
| Water | to 5 ml |

Injectable Suspension

| Compound of formula I | 100 mg |
|---|---|
| Polyvinyl pyrrolidone (RVP) | 170 mg |
| Tween 80 | 0.2% v/v |
| Methylhydroxybenzoate | 0.1% w/v |
| Water for injection | to 3 ml |

Capsule

| Compound of formula I | 100 mg |
|---|---|
| Starch 1500 | 150 mg |
| Magnesium stearate | 2.5 mg |
| filled into a soft gelatin capsule | |

We claim:

1. The trans compound of the formula (I):

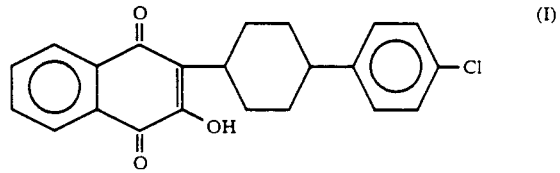

2. A physiologically acceptable salt of the trans compound of the formula (I):

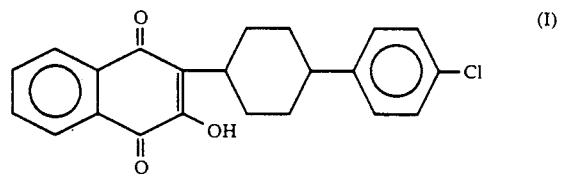

3. A method of treating malaria in a human having malaria comprising administering an effective malaria treatment amount of the trans compound of the formula (I):

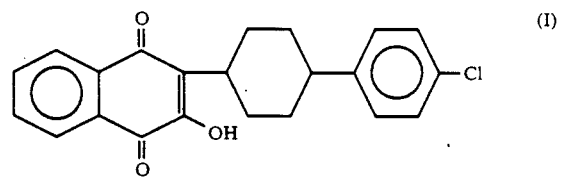

4. The method of claim 3, in which said compound or salt is administered in a capsule or in a tablet.

5. The method of claim 3, in which said compound or salt is administered by injection.

6. A tablet or capsule containing the trans compound of the formula (I):

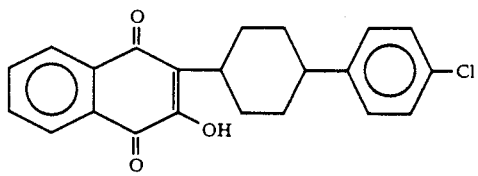

or a physiologically acceptable salt thereof, said tablet or capsule containing 10 mg to 1 gram of said compound or salt thereof.

7. A parenteral injectable preparation comprising the trans compound of the formula (I):

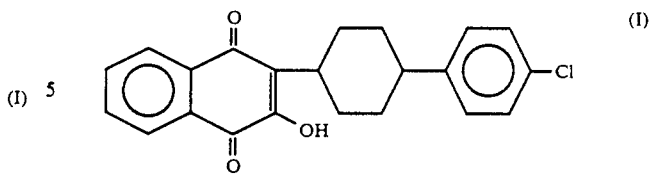

or a physiologically acceptable salt thereof and a pharmaceutically acceptable liquid carrier therefore.

8. A pharmaceutical preparation comprising the trans compound of the formula (I):

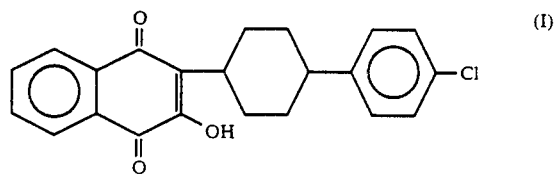

or a pharmacologically acceptable salt thereof together with a pharmaceutically acceptable carrier therefore.

* * * * *